United States Patent
Sue et al.

(10) Patent No.: US 11,928,820 B2
(45) Date of Patent: Mar. 12, 2024

(54) SYSTEMS AND METHODS FOR ANALYZING ELECTRONIC IMAGES FOR QUALITY CONTROL

(71) Applicant: PAIGE.AI, Inc., New York, NY (US)

(72) Inventors: Jillian Sue, New York, NY (US); Razik Yousfi, Brooklyn, NY (US); Peter Schueffler, Munich (DE); Thomas Fuchs, New York, NY (US); Leo Grady, Darien, CT (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 18/174,284

(22) Filed: Feb. 24, 2023

(65) Prior Publication Data

US 2023/0222662 A1   Jul. 13, 2023

Related U.S. Application Data

(63) Continuation of application No. 17/457,268, filed on Dec. 2, 2021, now Pat. No. 11,615,534, which is a
(Continued)

(51) Int. Cl.
*G06K 9/00* (2022.01)
*G06T 7/00* (2017.01)
(Continued)

(52) U.S. Cl.
CPC ........... *G06T 7/0014* (2013.01); *G16H 30/40* (2018.01); *G16H 50/20* (2018.01); *G16H 70/60* (2018.01);
(Continued)

(58) Field of Classification Search
None
See application file for complete search history.

(56) References Cited

U.S. PATENT DOCUMENTS

| 10,573,003 B2 | 2/2020 | Sethi et al. |
| 2016/0042511 A1 | 2/2016 | Chukka et al. |

(Continued)

FOREIGN PATENT DOCUMENTS

| CA | 3034900 A1 | 3/2018 |

OTHER PUBLICATIONS

Campanella, Gabriele, et al. "Towards machine learned quality control: A benchmark for sharpness quantification in digital pathology." Computerized Medical Imaging and Graphics 65 (2018): 142-151.

(Continued)

*Primary Examiner* — Wei Wen Yang
(74) *Attorney, Agent, or Firm* — Bookoff McAndrews, PLLC

(57) ABSTRACT

Systems and methods are disclosed for receiving a digital image corresponding to a target specimen associated with a pathology category, determining a quality control (QC) machine learning model to predict a quality designation based on one or more artifacts, providing the digital image as an input to the QC machine learning model, receiving the quality designation for the digital image as an output from the machine learning model, and outputting the quality designation of the digital image. A quality assurance (QA) machine learning model may predict a disease designation based on one or more biomarkers. The digital image may be provided to the QA model which may output a disease designation. An external designation may be compared to the disease designation and a comparison result may be output.

20 Claims, 10 Drawing Sheets

Related U.S. Application Data continuation of application No. 17/126,596, filed on Dec. 18, 2020, now Pat. No. 11,222,424.

(60) Provisional application No. 62/957,517, filed on Jan. 6, 2020.

(51) Int. Cl.
    *G16H 30/40*    (2018.01)
    *G16H 50/20*    (2018.01)
    *G16H 70/60*    (2018.01)

(52) U.S. Cl.
    CPC .............. *G06T 2207/10056* (2013.01); *G06T 2207/20081* (2013.01); *G06T 2207/30024* (2013.01); *G06T 2207/30168* (2013.01)

(56) References Cited

U.S. PATENT DOCUMENTS

| | | |
|---|---|---|
| 2019/0340468 A1 | 11/2019 | Stumpe et al. |
| 2020/0126207 A1 | 4/2020 | Saltz et al. |
| 2020/0272864 A1 | 8/2020 | Faust et al. |
| 2020/0273559 A1* | 8/2020 | Yousfi .................. G06T 17/20 |
| 2020/0365268 A1 | 11/2020 | Michuda et al. |
| 2020/0405225 A1 | 12/2020 | Kennedy et al. |
| 2021/0090694 A1 | 3/2021 | Colley et al. |

OTHER PUBLICATIONS

Owens, Scott R., et al. "Initial experience with a novel pre-sign-out quality assurance tool for review of random surgical pathology diagnoses in a subspecialty-based university practice." The American journal of surgical pathology 34.9 (2010): 1319-1323.

* cited by examiner

SYSTEMS AND METHODS FOR ANALYZING ELECTRONIC IMAGES FOR QUALITY CONTROL

RELATED APPLICATION(S)

This application is a continuation of and claims the benefit of U.S. application Ser. No. 17/457,268, filed Dec. 2, 2021, which is a continuation of U.S. application Ser. No. 17/126,596, filed Dec. 18, 2020, which claims priority to U.S. Provisional Application No. 62/957,517, filed Jan. 6, 2020, each of which are hereby incorporated herein by reference in their entireties.

FIELD OF THE DISCLOSURE

Various embodiments of the present disclosure relate generally to image-based specimen quality control (QC) and related image processing methods for quality assurance (QA). More specifically, particular embodiments of the present disclosure relate to systems and methods for processing images to provide QC feedback before specimen are evaluated, and also to provide QA to supplement specimen evaluation and diagnosis.

BACKGROUND

Laboratory quality control and digital pathology quality assurance are critical to the successful intake, processing, diagnosing, and archiving of patient specimens. Current methods for quality assurance include (1) second review of first-time diagnosis cancer cases, (2) periodic reviews of discordant or changed diagnoses by a quality assurance committee, or (3) random review of a subset of cases. These methods are non-exhaustive, mostly retrospective, and manual.

Conventional techniques for quality control and assurance can be improved with more systematic quality control and assurance. However, systematic quality assurance is impractical and inefficient today because it would require duplicative efforts by two pathologists. Such duplicative efforts would be prohibitively resource and time-intensive. As a result, a desire exists for feasible systemic quality control and assurance.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for implementing QC and QA measures to digital pathology images.

A method for outputting quality designations includes receiving a digital image corresponding to a target specimen associated with a pathology category, wherein the digital image is an image of human tissue and/or an image algorithmically generated to replicate human tissue, determining a quality control (QC) machine learning model, the QC machine learning model generated by processing a plurality of training images, associated with the pathology category, to predict a quality designation based on one or more artifacts, providing the digital image as an input to the QC machine learning model, receiving the quality designation for the digital image as an output from the machine learning model, and outputting the quality designation of the digital image.

A method for verifying disease designations includes receiving at least one digital image corresponding to a target specimen associated with a pathology category, wherein the digital image is an image of human tissue and/or an image algorithmically generated to replicate human tissue, determining a quality assurance (QA) machine learning model, the QA machine learning model generated by processing a plurality of training images, from the pathology category, to predict a disease designation based on one or more biomarkers, providing the digital image as an input to the QA machine learning model, receiving the disease designation for the digital image as an output from the QA machine learning model, receiving an external designation for the digital image, comparing the disease designation to the external designation, and outputting a comparison result based on comparing the disease designation to the external designation.

A system for verifying disease designations includes a memory storing instructions and a processor executing the instructions to perform a process including receiving at least one digital image corresponding to a target specimen associated with a pathology category, wherein the digital image is an image of human tissue and/or an image algorithmically generated to replicate human tissue, determining a quality assurance (QA) machine learning model, the QA machine learning model generated by processing a plurality of training images, from the pathology category, to predict a disease designation based on one or more biomarkers, providing the digital image as an input to the QA machine learning model, receiving the disease designation for the digital image as an output from the QA machine learning model, receiving an external designation for the digital image, comparing the disease designation to the external designation, and outputting a comparison result based on comparing the disease designation to the external designation.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
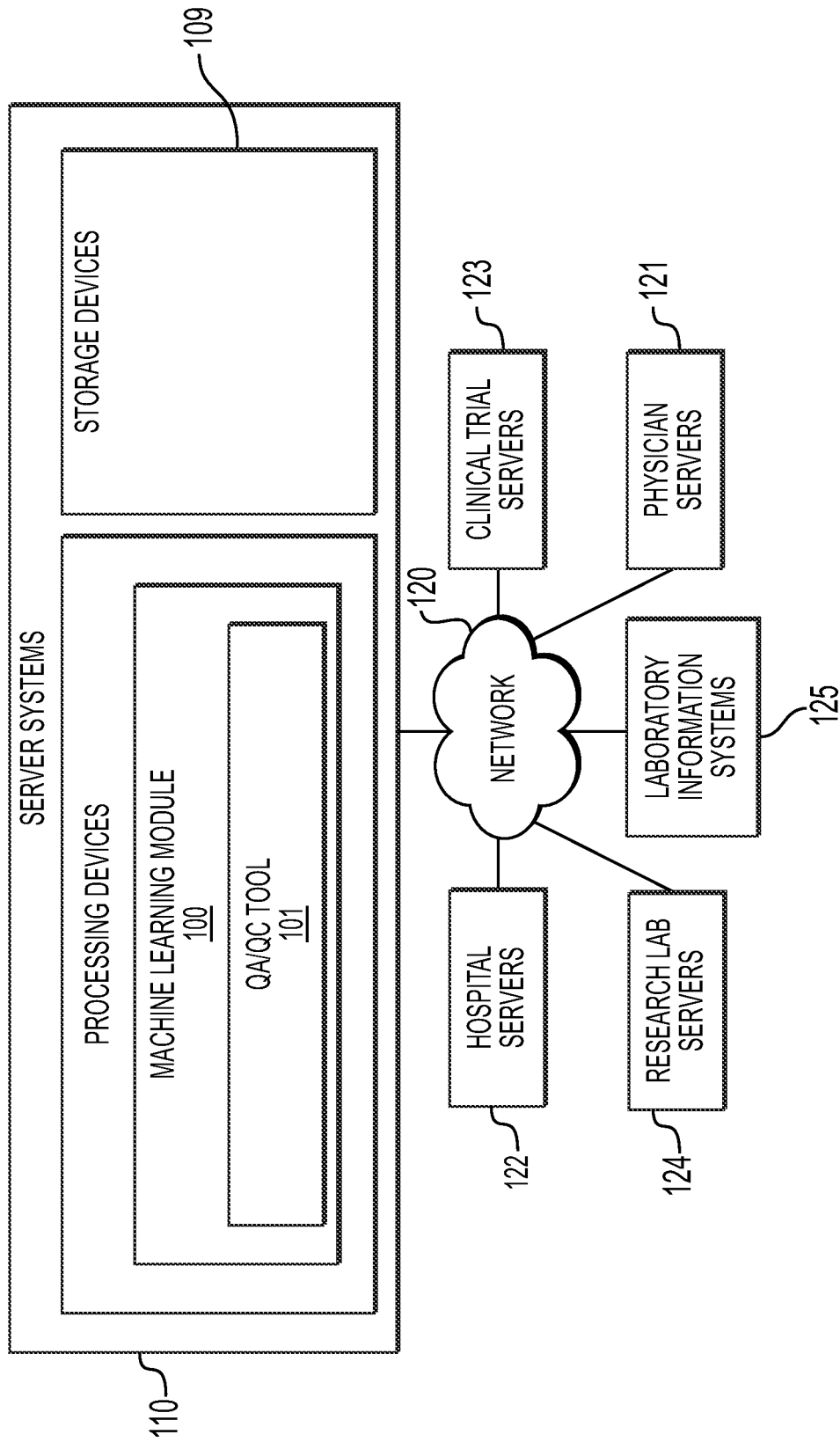
FIG. 1A illustrates an exemplary block diagram of a system and network for implementing QA/QC tools with digital images, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) that may contain the additional information for the pathologist to use in making a diagnosis. This process of creating additional slides may be time-consuming, not only because it may involve retrieving the block of tissue, cutting it to make a new slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. The present disclosure presents a consolidated workflow for improving diagnosis of cancer and other diseases. The workflow may integrate, for example, slide evaluation, tasks, image analysis and cancer detection artificial intelligence (AI), annotations, consultations, and recommendations in one workstation. In particular, the present disclosure describes various exemplary AI tools that may be integrated into the workflow to expedite and improve a pathologist's work.

For example, computers may be used to analyze an image of a tissue sample to quickly identify whether the quality of the tissue sample is sufficient for its intended purpose (i.e., quality control) and may further analyze the image of the tissue sample to determine an outcome to supplement a determination made by another entity, such as a pathologist (i.e., quality assurance). Thus, the process of obtaining stained slides and tests may be done automatically before being reviewed by a pathologist. When paired with automatic slide quality review and result determination, this may provide a fully automated slide preparation and evaluation pipeline in parallel with a pathologist review. This automation has, at least, the benefits of (1) minimizing an amount of time wasted by a pathologist determining the findings of a slide by using slides that do not meet a quality threshold (2) minimizing the (average total) time from specimen acquisition to diagnosis by avoiding the additional time conducting manual analysis or questionable slides, (3) reducing the amount of repeat tissue evaluation by automatically determining slide quality prior to it being presented for pathologist review, (4) reducing the cost of repeated biopsies and pathologist review by providing slides that meet a quality threshold, (5) eliminating or mitigating the need for a second or subsequent pathologist diagnostic review, (6) reducing the probability of an incorrect diagnosis, (7) increase the probability of a proper diagnosis based on a dual confirmation, and/or (8) identifying or verifying correct properties (e.g., pertaining to a specimen type) of a digital pathology image.

The process of using computers to assist pathologists is called computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Haemotoxylin and Eosin (H&E). For medical diagnosis, H&E is a widely used dye-based method, with hematoxylin staining cell nuclei blue, eosin staining cytoplasm and extracellular matrix pink, and other tissue regions taking on variations of these colors. In many cases, however, H&E-stained histologic preparations do not provide sufficient information for a pathologist to visually identify biomarkers that can aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues enabling the visual detection of cells expressing specific proteins of interest, which can reveal biomarkers that are not reliably identifiable to trained pathologists based on the analysis of H&E-stained slides. ISH and FISH may be employed to assess the number of copies of genes or the abundance of specific RNA molecules, depending on the type of probes employed (e.g. DNA probes for gene copy number and RNA probes for the assessment of RNA expression). If these methods also fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect. Computational processes using machine learning models and devices may be used to assist pathologists in detecting abnormalities that may otherwise be difficult to detect. For example, AI may be used to predict biomarkers (such as the over-expression of a protein and/or gene product, amplification, or mutations of specific genes) from salient regions within digital images of tissues stained using H&E and other dye-based methods. The images of the tissues could be whole slide images (WSI), images of tissue cores within microarrays or selected areas of interest within a tissue section. Using staining methods like H&E, these biomarkers may be difficult for humans to visually detect or quantify without the aid of additional testing. Using AI to infer these biomarkers from digital images of tissues has the potential to improve patient care, while also being faster and less expensive.

As described above, computational pathology processes and devices of the present disclosure may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

Implementations of the disclosed subject matter include systems and methods for systematic QC for pathology specimen preparation and QA for quality of diagnoses, throughout a histopathology workflow. With an automated and systematic QC and QA mechanism, quality can be ensured throughout the workflow of every case. Systematic QC and QA has the potential to provide efficiencies and improve diagnostic quality.

In a detection-based workflow and quality system disclosed herein, the input to the system may include one or multiple digitized pathology image(s) and any relevant additional inputs. Outputs of the system may include global and/or local information about the specimen, with respect to quality control and assurance.

According to an implementation, a QC machine learning model may be generated to determine the quality of digitized pathology images. The qualification may include generating a quality designation for each digitized pathology image where the quality designation is either an approved designation or a rejected designation. An approved designation may result from a QC machine learning model output that indicates that no artifacts were found in the digitized pathology image or that no found artifacts exceed an applicable artifact threshold. A rejected designation may result from a QC machine learning model output that indicates that an artifact or an artifact amount above an applicable artifact threshold was found.

The QC machine learning model may be trained based on supervised, partially supervised, or unsupervised training images from the same pathology category as the respective digitized pathology images input to the QC machine learning model. Pathology categories may include, but are not limited to, histology, cytology, frozen section, immunohistochemistry, or the like. The QC machine learning model may detect the presence, absence, or extent of artifacts including scanning results or errors (e.g., blur, missing tissue, lines, etc.) and/or from tissue preparation (e.g. missing or folded tissue, bubbles, cracks in glass, scratches, dust, pen, over stain, etc.).

According to an implementation, a QA machine learning model may be generated to output disease designations based on digitized pathology images received as inputs to the model. The disease designations may be one or more of cancer detection, cancer grade, cancer origin, diagnosis, a presence or absence of a microorganism, specimen type, cancer type, cancer status, tumor size, lesions risk level, and/or grade. The QA machine learning model disease designations may be compared to an external designation and the comparison result may be a match or a discrepancy designation (e.g., if no match is detected). If a discrepancy designation is determined, a discrepancy level may be determined and, based on the discrepancy level, either a warning or a trigger may be generated. The external designation may be based on a designation made by a pathologist, a third-party institution, and/or by a system other than the QA machine learning model.

A trigger based on a discrepancy level may initiate a manual re-designation of the digital pathology image or generation of an alert that informs applicable individuals or entities about the discrepancy.

The QA machine learning model may be trained based on supervised, partially supervised, or unsupervised training images, biomarkers, patient information, and applicable designation outputs. Inputs to a generated QA machine learning mode may be digital pathology images from one or more pathology categories such as histology, cytology, frozen section, or immunohistochemistry.

Notifications, visual indicators, and/or reports may be generated based on the output of the QC and/or the QA machine learning models, as further disclosed herein. The reports may be based on an individual digitized image or based on a plurality of digitized images either during a given time period or generally retrospectively.

The systems disclose herein may be implemented locally (e.g., on-premises) and/or be remote (e.g., cloud-based). The systems may or may not have user-interface(s) and workflows that pathologist(s) may directly accesses (e.g., a downstream oncologist could be flagged that there was a discrepancy, notifications to care team, etc.). Accordingly, implementations disclosed herein may be used as stand-alone operations, or used within a digital workflow. In use, the disclosed systems may perform QA/QC analysis and delivery before or after a received diagnosis (e.g., by a pathologist). Implementations disclosed herein may be performed in real-time (e.g., if slides are immediately sent from scanner to a QA or QC machine learning model) or may be run in batch mode, where discrepancies may be logged and/or reported.

While the disclosed subject matter is described as implemented based on oncology applications, they may be used for other forms of disease (e.g., infectious diseases, detection processes, or the like that use digital images for diagnostic purposes. In addition to providing QC/QA benefits, the described implementations may be used for training health care professionals (e.g., slide technicians, pathologists, etc.) to practice slide generation and/or diagnosis determination, while reducing the risk of patient harm.

FIG. 1A illustrates a block diagram of a system and network for determining specimen property or image property information pertaining to digital pathology image(s), using machine learning, according to an exemplary embodiment of the present disclosure. As further disclosed herein, the system and network of FIG. 1A may include a machine learning model with QA/QC tools to evaluate the quality of digital images and/or determine disease diagnosis for assuring the quality of an external diagnosis.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an implementation, the electronic network 120 may also be connected to server systems 110, which may include processing devices that are configured to implement a machine learning module 100, in accordance with an exemplary embodiment of the disclosed subject matter.

The physician servers 121, hospital servers 122, clinical trial servers 123, research lab servers 124, and/or laboratory information systems 125 may create or otherwise obtain images of one or more categories of pathology specimens including patients' cytology specimen(s), histopathology specimen(s), slide(s) of the cytology specimen(s), histology, immunohistochemistry, digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities via the machine learning module 100. For example, the processing devices may include QA tools and/or QC tools (collectively referred to as QA/QC tools 101), as shown as machine learning module 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a LIS 125.

Figure 1B:
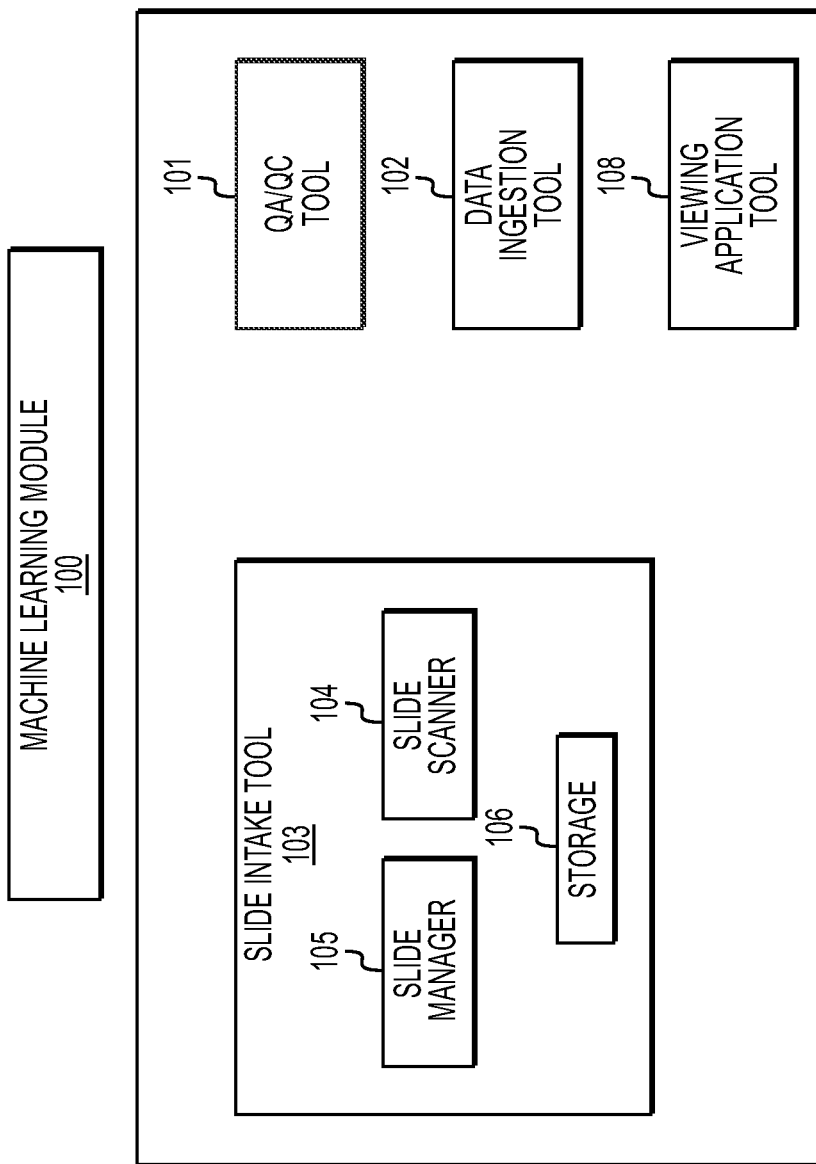
FIG. 1B illustrates an exemplary block diagram of a machine learning model, according to an exemplary embodiment of the present disclosure.

FIG. 1B illustrates an exemplary block diagram of a machine learning module 100 for determining specimen property or image property information pertaining to digital pathology image(s), using machine learning.

Specifically, FIG. 1B depicts components of the machine learning module 100, according to one embodiment. For example, the machine learning module 100 may include a QA/QC tool 101, a data ingestion tool 102, a slide intake tool 103, a slide scanner 104, a slide manager 105, a storage 106, and a viewing application tool 108. For clarification, the machine learning module 100 shown in FIGS. 1A and 1B is a previously trained and generated machine learning model (e.g., a QA machine learning model, a QC machine learning model, etc.). Additional disclosure is provided herein for training and generating different types of machine learning models that may be used as machine learning module 100.

The QA/QC tool 101, as described herein, refers to a process and system for determining a characteristic (e.g., artifact, biomarker, etc.) to determine image quality and/or disease designations pertaining to digital pathology image(s) using a machine learning model such as a QA machine learning model or QC machine learning model. The QA/QC tool 101 may include a plurality of machine learning models or may load one machine learning model at a time.

The data ingestion tool 102 refers to a process and system for facilitating a transfer of the digital pathology images to the various tools, modules, components, and devices of the machine learning module 100 that are used for characterizing and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with a characterization or image property information pertaining to digital pathology images, according to an exemplary embodiment. The information may be provided through various output interfaces (e.g., a screen, a monitor, a storage device, and/or a web browser, etc.). As an example, the viewing application tool 108 may apply an overlay layer over a digital pathology image and the overlay layer may highlight key areas of consideration. The overlay layer may be or may be based on the output of the QA/QC tool 101 of the machine learning module 100. As further discussed herein, the viewing application tool 108 may be used to show artifacts based on the output of a QC machine learning model and/or may be used to show biomarkers based on the output of a QA machine learning model.

The QA/QC tool 101, and each of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the QA/QC tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

The QA/QC tool 101 may provide the output of the machine learning module 100 (e.g., a quality designation, disease designation, comparison result, etc.). As an example, the slide intake tool 103 and the data ingestion tool 102 may receive inputs to the machine learning module 100 and the QA/QC tool 101 may identify artifacts and/or biomarkers in the slides based on the data, and output an image highlighting the artifacts and/or biomarkers via the viewing application tool 108.

Any of the above devices, tools, and modules may be located on a device that may be connected to an electronic network 120, such as the Internet or a cloud service provider, through one or more computers, servers, and/or handheld mobile devices.

Figure 2A:
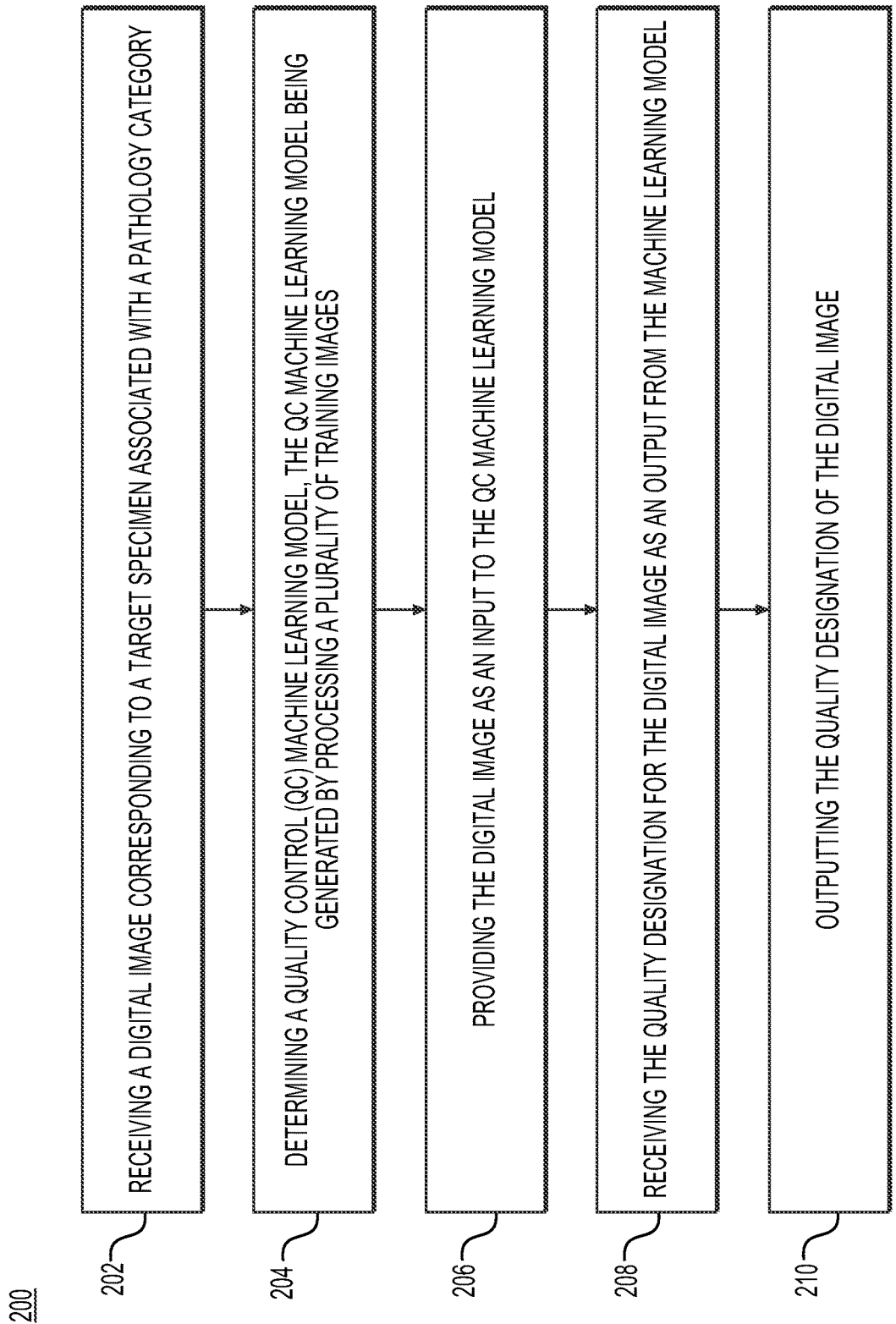
FIG. 2A is a flowchart illustrating an exemplary method for using a QC machine learning model, according to an exemplary embodiment of the present disclosure.

FIG. 2A shows a flowchart 200 for outputting quality designations for digital images, in accordance with exemplary implementations of the disclosed subject matter. At 202 of FIG. 2A, a digital image corresponding to a target specimen associated with a pathology category may be received. The digital image may be a digital pathology image captured using the slide intake tool 103 of FIG. 1B. At 204, a QC machine learning model may be received (e.g., at the machine learning module 100). The QC machine learning model may be trained by processing a plurality of training images that are from the same pathology category as the digital image received at 202. The pathology categories may include, but are not limited to histology, cytology, frozen section, or immunohistochemistry. At 206, the digital image from 202 may be provided to the QC machine learning model as an input to the model. One or more other attributes may also be provided as an input to the QC machine learning model. The one or more other attributes may include, but are not limited to, a pathology category, a slide type, a glass type, a tissue type, a tissue region, a chemical used, a stain amount, time applied, scanner type, date, or the like. At 208, the QC machine learning model may output a quality designation for the digital image. The quality designation may be an approval or a rejection and may also include a scale such as an approval scale and/or a rejection scale that provides a finer indication of the quality of the digital image provided at 202 and as an input to the QC machine learning model at 206. At 210, the quality designation may be output as a data signal, a report, a notification, an alert, a visual output (e.g., via viewing application tool 108), or the like.

As shown in FIG. 2A, a digital image corresponding to a target specimen associated with a pathology category may be received at 202. The target specimen may be a biopsied or otherwise retrieved tissue sample retrieved from a patient. The target specimen may be retrieved during a surgical procedure where a portion of a patient's tissue is retrieved from the patient's body for analysis. The target specimen may be a portion or subset of the total amount of tissue extracted from the patients such that multiple specimen slides may be generated from the tissue extracted from a single procedure.

The target specimen may be associated with at least one pathology category such as histology, cytology, frozen section, or immunohistochemistry, as disclosed herein. According to an implementation, the pathology category and other image information about the digital image or target specimen may also be received. The image information may include, but is not limited to a slide type, a glass type, a tissue type, a tissue region, a chemical used, and a stain amount.

At 204, a QC machine learning model may be received. The QC machine learning model may be trained and generated at the machine learning module 100 or may be trained and generated externally and be received at the machine learning module 100. The QC machine learning model may be trained by processing a plurality of training images that are from the same pathology category as the digital image received at 202. The pathology categories may include, but are not limited to histology, cytology, frozen section, or immunohistochemistry. The QC machine learning model may be instantiated using deep learning. The QC machine learning model may use information about an entire digital pathology image, e.g., the specimen type, the overall quality of the cut of the specimen, the overall quality of the glass slide itself, or tissue morphology characteristics, and determine an overall quality designation for digital pathology images.

The QC machine learning model may detect artifacts associated with a digital image based on an analysis of properties of the digital image. The artifacts may be detected based on applying one or more digital or mathematical filters, scanning techniques (e.g., pixel by pixel scanning), pixel comparison technique (e.g., comparing one set of pixels to another), or the like. The artifacts that the QC machine learning model may be trained to identify may include, but are not limited to artifacts including scanning results or errors (e.g., blur, missing tissue, lines, etc.) and/or from tissue preparation (e.g. missing or folded tissue, bubbles, cracks in glass, scratches, dust, pen, over stain, etc.).

To generate the QC machine learning model at 204, a training dataset including a large plurality of digital pathology images of pathology specimens (e.g., histology, cytology, immunohistochemistry, etc.) may be received. The digital pathology images may be digital images generated based on physical biopsy samples, as disclosed herein, or may be images that are algorithmically generated to replicate human tissue by, for example, a rendering system or a generative adversarial model. Image or specimen associated information (e.g., slide type, a glass type, a tissue type, a tissue region, a chemical used, a stain amount, time applied, scanner type, date, etc.) may also be received as part of the training dataset. Additionally, as part of training the QC machine learning model, each image may be paired with output information about the known or assumed quality of the digital image or corresponding specimen. Such output information may include known or assumed artifact information, expected quality information, or the like. For example, a given image may be provided as a training image and may be known to have a folded tissue as part of the digital image. The image and an indication about the presence, location, and or extent of the fold may be provided and paired with the image. The QC machine learning model may learn from a plurality of such training images and associated information such that the QC machine learning model's parameters are trained (e.g., fit) to be capable of detecting the presence, absence, or degree of an artifact detected in each training image. Although a supervised training is provided as an example, it will be understood that the training of the QC machine learning model may be partially or unsupervised.

The training dataset including the digital pathology images, the image or specimen associated information, and/or the output information may be generated and/or provided by one or more of the systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc., and/or (b) digitized tissue samples from a 3D imaging device, such as microCT.

The QC machine learning model may be generated based on applying the digital pathology images with, optionally, the associated information paired with the output information as applied by a machine learning algorithm. The machine learning algorithm may accept, as inputs, the pathology specimens, the associated information, and the output information and implement training using one or more techniques. For example, the QC machine learning model may be trained in one or more Convolutional Neural Networks (CNN), CNN with multiple-instance learning or multi-label multiple instance learning, Recurrent Neural Networks (RNN), Long-short term memory RNN (LSTM), Gated Recurrent Unit RNN (GRU), graph convolution networks, or the like or a combination thereof. Convolutional neural networks can directly learn the image feature representations necessary for discriminating among characteristics, which can work extremely well when there are large amounts of data to train on for each specimen, whereas the other methods can be used with either traditional computer vision features, e.g., SURF or SIFT, or with learned embeddings (e.g., descriptors) produced by a trained convolutional neural network, which can yield advantages when there are only small amounts of data to train on. The trained QC machine learning model may be configured to provide quality designations for the digital pathology images.

Figure 3:
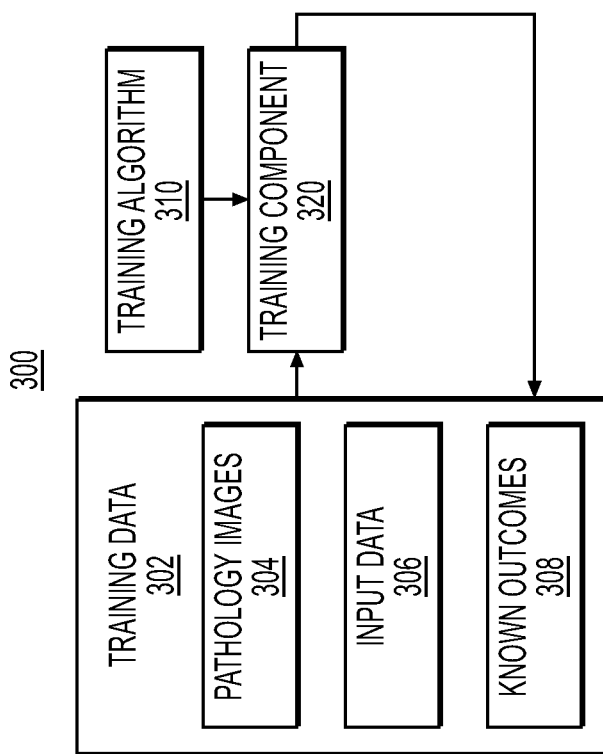
FIG. 3 illustrates an exemplary block diagram of a training module, according to an exemplary embodiment of the present disclosure.

FIG. 3 shows an example training module 300 to train either a QC machine learning model. As shown in FIG. 3, training data 302 may include one or more of pathology images 304 (e.g., digital representation of biopsied images), input data 306 (e.g., a digital pathology image dataset), and known outcomes 308 (e.g., quality designations) related to the input data 306. The training data 302 and a training algorithm 310 may be provided to a training component 320 that may apply the training data 302 to the training algorithm 310 in order to generate a QC machine learning model.

At 206, the QC machine learning model may be provided a patient based digital pathology image (e.g., a digital image of pathology specimen (e.g., histology, cytology, immunohistochemistry etc.)) as well as, optionally, associated information. After training, the QC machine learning mode may be applied to the digital pathology image and the associated information to determine a quality designation for the patient based digital pathology image at 208.

The quality designation may be an approval or rejection of the digital pathology image based on predetermined or dynamically determine thresholds. A dynamically determined threshold may be established based on the volume of digital images provided to the QC machine learning model. For example, the QC machine learning model may be set to reject the worst 10% of digital pathology images and, accordingly, the number of digital pathology images that are rejected may change based on the number of digital pathology images input to the model. As a result of the quality designation (e.g., a rejection), the target specimen may be re-prepared (e.g., in a lab) and/or the existing target specimen may be re-scanned. The specific action may be based on the artifact identified by the QC machine learning model such that a blur may indicate a scanning error and a re-scan may be initiated whereas a missing tissue may indicate a pathology sampling error and a new specimen may be re-prepared in a lab setting.

According to an implementation, the quality designation may be a quality score determination. The quality score may be indicative of QC issues (e.g., artifacts such as errors or imperfections) for digital pathology images at a global or local level and that may greatly affect the usability of a digital pathology image. The quality score may be determined in view of the number or extent of artifacts found in a given image. The quality score may be determined based on the training dataset used to train the QC machine learning model or may be determined relative to other digital pathology images provided as input to the QC machine learning model.

The output of the QC machine learning model (i.e., the quality designation), at 210, may be provided to a storage device 109 of FIG. 1A (e.g., cloud storage, hard drive, network drive, etc.). The output of the QC machine learning model may be or may also be a notification based on the quality characteristic. The notification may include information about the artifact such as the presence of one or more artifacts, the absence of any or specific artifacts, and/or a degree of one or more artifacts present in the digital pathology sample. The notification may be provided via any applicable technique such as a notification signal, a report, a message via an application, a notification via a device, or the like. The notification may be provided to any applicable device or personnel (e.g., histology technician, scanner operator, pathologist, record, etc.). As an example, the output of the QC machine learning model may be integrated with corresponding target specimen's history in, for example, the laboratory information systems 125 that stores a record of the patient and the associated target specimen.

According to an implementation, the output of the QC machine learning model may be a report based on the quality designation or the process for obtaining, using, and/or evaluating the digital pathology image. The report may be in any applicable format such as a PDF format, HTML format, in-app format, or the like. The report may include, for example, types of artifacts (e.g., errors) found, a number each type of artifact, clinical impact of artifacts, time to rectify artifacts, potential patterns or correlations in artifacts (e.g. a particular scanner which tends to generate artifacts, a particular staining type which tends to generate artifacts, a particular tissue source which tends to generate artifacts, etc.). The report may also include a workflow analysis such as overall turnaround times and/or quality of work. The report may also provide historically relevant information based on a plurality of digital pathology samples analyzed by the QC machine learning model. The historically relevant information may be generated based on factoring in the outputs of the plurality of digital pathology samples and the corresponding report may include an amendment rate, concordance rates, or the like.

According to an implementation, the output of the QC machine learning model, at 210, may be or may include a visual indicator. The visual indicator may be provided, for example, via the viewing application tool 108 of FIG. 1B. The visual indicator may highlight a given artifact as it relates to the digital pathology image. As an example, the visual indicator may be an overlay over the digital pathology image that highlights the location of the artifact, the type of artifact, the degree of a presence of the artifact, or the like.

According to an implementation, the QC machine learning algorithm may also be trained based on and/or receive as inputs clinical information (e.g. patient information, surgical information, diagnostic information, etc.), laboratory information (e.g. processing times, personnel, tests, etc.). The QC machine learning algorithm may provide a quality designation based on such inputs. Additionally, the QC machine learning algorithm may provide alternative or additional outputs such as a processing score, a personnel evaluation, or the like.

As further disclosed herein, the QC machine learning algorithm may be integrated within a pipeline of a clinical workflow for generating, analyzing, and/or reviewing digital pathology images.

Figure 2B:
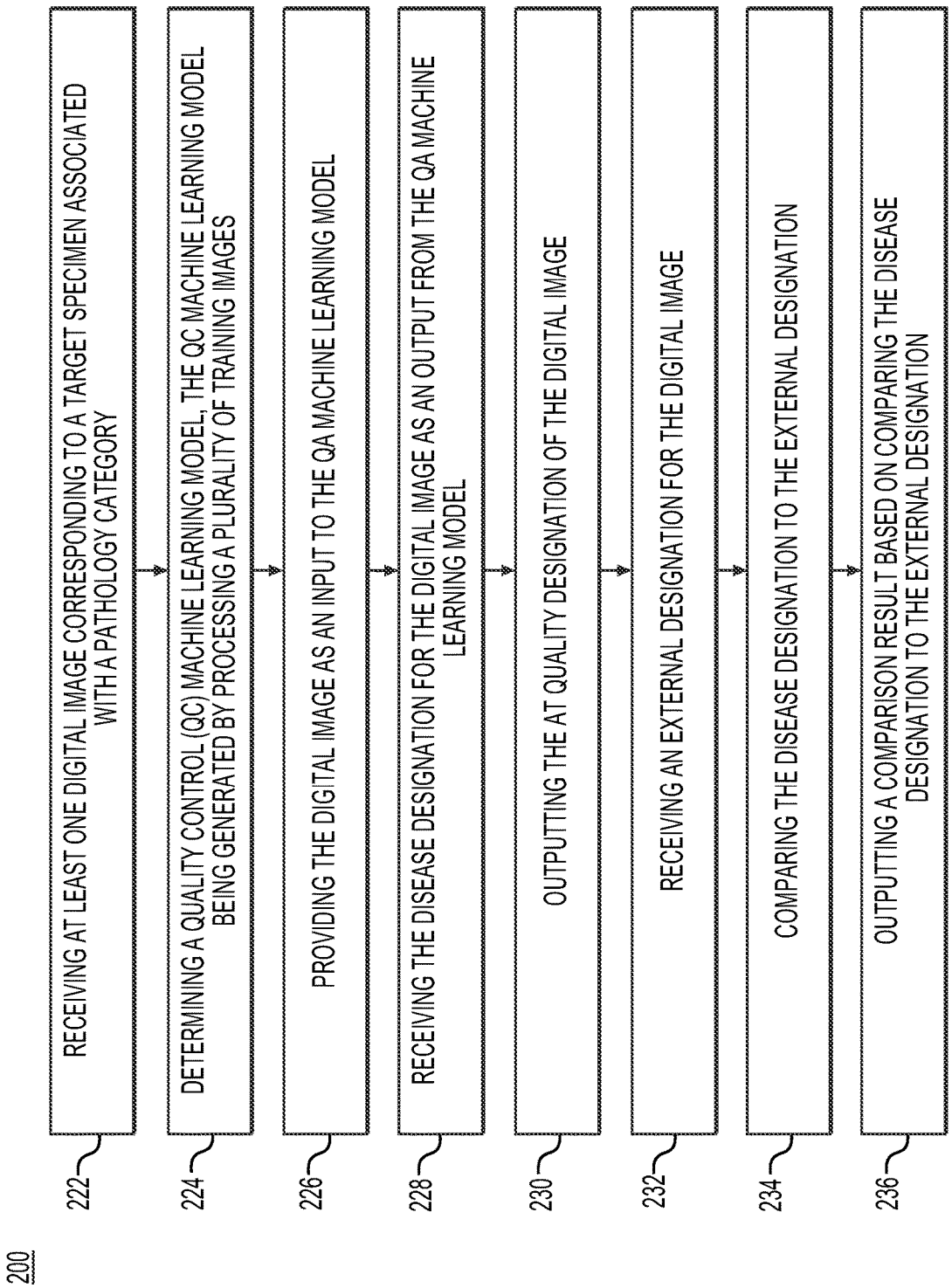
FIG. 2B is a flowchart illustrating an exemplary method for using a QA machine learning model, according to an exemplary embodiment of the present disclosure.

FIG. 2B shows a flowchart 220 for generating disease designations based on digital pathology images and outputting comparison results based on comparing the disease designations to external designations, in accordance with exemplary implementations of the disclosed subject matter. At 222 of FIG. 2B, a digital image corresponding to a target specimen associated with a pathology category may be received. The digital image may be a digital pathology image captured using the slide intake tool 103 of FIG. 1B. At 224, a QA machine learning model may be received (e.g., at the machine learning module 100). The QA machine learning model may be trained by processing a plurality of training images that are from the same pathology category as the digital image received at 222. The pathology categories may include, but are not limited to histology, cytology, frozen section, or immunohistochemistry. At 226, the digital image from 222 may be provided to the QA machine learning model as an input to the model. One or more other attributes may also be provided as an input to the QC machine learning model. The one or more other attributes may include, but are not limited to, slide based attributes, patient attributes, tissue attributes, or the like. At 228, the QA machine learning model may output a disease designation for the digital image. The disease designation may be generated based on detection of one or more biomarkers and may include one or more of a cancer detection, cancer grade, cancer origin, diagnosis, a presence or absence of a microorganism, specimen type, cancer type, cancer status, tumor size, lesions risk level, grade, or the like. At 230, an external designation for the target specimen may be received. The external designation may be based on the digital image received at 222 or the target specimen based on which the digital image was based on. At 232, the disease designation may be compared to the external designation and at 234 the comparison result based on comparing the disease designation to the external designation may be output. The comparison result may be output as a data signal, a report, a notification, an alert, a visual output (e.g., via viewing application tool 108), or the like.

As shown in FIG. 2B, a digital image corresponding to a target specimen associated with a pathology category may be received at 222. The target specimen may be a biopsied or otherwise retrieved tissue sample retrieved from a patient. The target specimen may be retrieved during a surgical procedure where a portion of a patient's tissue is retrieved from the patient's body for analysis. The target specimen may be a portion or subset of the total amount of tissue extracted from the patients such that multiple specimen slides may be generated from the tissue extracted from a single procedure.

The target specimen may be associated with at least one pathology category such as histology, cytology, frozen section, or immunohistochemistry, as disclosed herein. According to an implementation, the pathology category and other image information about the digital image or target specimen may also be received. The image information may include, but is not limited to a slide type, a glass type, a tissue type, a tissue region, a chemical used, and a stain amount.

At 224, a QA machine learning model may be received. The QA machine learning model may be trained and generated at the machine learning module 100 or may be trained and generated externally and be received at the machine learning module 100. The QC machine learning model may be trained by processing a plurality of training images that are from the same pathology category as the digital image received at 202. The QA machine learning model may detect the presence or absence of cancer across more than one tissue type (e.g., prostate cancer, breast cancer, bladder cancer, etc.). It may also detect additional biomarkers or information important for staging. For example, for bladder cancer, the generalized machine learning model may output the presence or absence of muscularis propria, a muscle that needs to be detected for bladder cancer staging. The QA machine learning model may be trained with large amounts of data to predict disease, biomarkers, and other attributes relevant to cancer treatment from multiple tissue types. Through this process, it may detect the presence of cancer and/or biomarkers across a wide array of different tissue types such that its layers are built upon an understanding of tumor characteristics as well as normal and abnormal tissue morphology.

The QA machine learning model may be generated based on a patient dataset including a large plurality of digital images of pathology specimens (e.g., histology, cytology, immunohistochemistry, etc.). The pathology specimens may be digital images generated based on physical biopsy samples, as disclosed herein, or may be images that are algorithmically generated to replicate human tissue by, for example, a rendering system or a generative adversarial model. Patient associated information (genomic information, lab tests, radiology, patient characteristics, patient information, treatment information, etc.) may also be received as part of the patient dataset to train the QA machine learning model. Additionally, as part of training the QA machine learning model, each patient dataset may be paired with information or indications about a cancer characteristic outputs (e.g., biomarkers) such as disease presence/absence, presence of staging variables (e.g., muscularis propria for bladder cancer), classification of the form of cancer (e.g., lobular or ductal for breast cancer), and other relevant variables for different cancer types, outcome status (e.g., response, recurrence, etc.) and/or the presence of any biomarkers.

The patient dataset, patient associated information, and/or the cancer characteristic outputs may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The QA machine learning model may be generated based on applying the patient dataset and the patient associated information paired with the cancer characteristic output to a machine learning algorithm. The machine learning algorithm may accept, as inputs, the pathology specimens, the patient associated information, and the cancer characteristic outputs and implement training using one or more techniques. For example, the generalized machine learning model may be trained in one or more Convolutional Neural Networks (CNN), CNN with multiple-instance learning or multi-label multiple instance learning, Recurrent Neural Networks (RNN), Long-short term memory RNN (LSTM), Gated Recurrent Unit RNN (GRU), graph convolution networks, or the like or a combination thereof. Convolutional neural networks can directly learn the image feature representations necessary for discriminating among characteristics, which can work extremely well when there are large amounts of data to train on for each specimen, whereas the other methods can be used with either traditional computer vision features, e.g., SURF or SIFT, or with learned embeddings (e.g., descriptors) produced by a trained convolutional neural network, which can yield advantages when there are only small amounts of data to train on. The trained QA machine learning model may be configured to provide disease designations (e.g., cancer characteristics) as outputs based on patient data and patient associated information.

FIG. 3 shows an example training module 300 to train either the QA machine learning model. As shown in FIG. 3, training data 302 may include one or more of pathology images 304 (e.g., digital representation of biopsied images), input data 306 (e.g., a patient dataset, patient associated information, etc.), and known outcomes 308 (e.g., cancer characteristics) related to the input data 306. The training data 302 and a training algorithm 310 may be provided to a training component 320 that may apply the training data 302 to the training algorithm 310 in order to generate a machine learning model.

The QA machine learning model may receive a patient dataset such as one or more digital pathology images (e.g., histology, cytology, immunohistochemistry etc.) at 226. According to an implementation, the QA machine learning model may also receive patient associated information (e.g., genomic, lab tests, radiology, patient characteristics etc.). After training, the QA machine learning model may be applied to the patient dataset and the patient associated information to determine one or more disease designations at 228. A disease designation may be one or more of cancer detection, cancer grade, cancer origin, diagnosis, a presence or absence of a microorganism, specimen type, cancer type, cancer status, tumor size, lesions risk level, grade, or the like. The disease designations may not be cancer specific such that the QA machine learning model may provide disease designations across cancer types, if any.

The output of the QA machine learning model (i.e., the one or more disease designations) may be provided to a storage device 109 of FIG. 1A (e.g., cloud storage, hard drive, network drive, etc.). The storage device 109 of may store one or more other disease designations from previous digital pathology image inputs.

At 230, an external designation associated with the digital image may be received. The external designation may be one or more of cancer detection, cancer grade, cancer origin, diagnosis, a presence or absence of a microorganism, specimen type, cancer type, cancer status, tumor size, lesions risk level, grade, or the like. The external designation may be based on the digital image or the target specimen based on which the digital image is generate.

The external designation may be a manual designation provided by a health care professional (e.g., a pathologist) based on a review of the digital image or the target specimen associated with the digital image. Alternatively or in addition, the external designation may be provided by a third-party (e.g., a third-party health care facility, a third-party system, a system not associated with the QA machine learning model, a different machine learning model, or the like) and, accordingly, may be a manual designation or an automated designation.

The external designation may be in a format that is comparable to the disease designation received at 228, such that the external designation may be compared to the disease designation at 232. The comparison may be conducted by comparing data points, comparing end results, text analysis, optical character recognition (OCR), or the like. Although a single comparison is discussed herein, it will be understood that multiple comparisons of a plurality of different attributes of the disease designation and/or the external designation may be made. For example, the disease designation and external designation may provide a cancer type and a cancer severity. Accordingly, both the cancer type and the cancer severity as provided by the respective disease designation and the external designation may be compared.

The comparison result may be output at 234 (i.e., the comparison result designation). The comparison result output may be provided to a storage device 109 of FIG. 1A (e.g., cloud storage, hard drive, network drive, etc.). The storage device 109 may also store previous comparison results between previous disease designations and external designations. The comparison result may be the difference between the output of the QA machine learning model and a health care professional's (e.g., pathologist's) subjective evaluation of the digital image or the associated target specimen and may confirm findings, flag errors, identify issues, or cause a review based on the comparison result.

The comparison results output at 234 may be or may also be a notification. The notification may include information about similarities between the disease designation (i.e., output from the QA machine learning model) and the external designation, differences between the disease designation and the external designation, degrees of differences or similarities between the disease designation and the external designation, or the like. The notification may be provided via any applicable technique such as a notification signal, a report, a message via an application, a notification via a device, or the like. The notification may be provided to any applicable device or personnel (e.g., histology technician, scanner operator, pathologist, record, etc.). As an example, the comparison result may be integrated with corresponding target specimen's history in, for example, the laboratory information systems 125 that stores a record of the patient and the associated target specimen.

According to an implementation, the comparison result may be presented as a report based on the similarities, differences, and/or degree of similarity or differences between the disease designation and the external designation. The report may be in any applicable format such as a PDF format, HTML format, in-app format, or the like. The report may include, for example, types of results found, overlapping results between the disease designation and the external designation, contradictory results between the disease designation and the external designation, clinical impact of similarities or differences, time to rectify differences, potential patterns or correlations in the comparison, or the like. The report may also include a workflow analysis such as overall turnaround times and/or quality of work. The report may also provide historically relevant information based on a plurality of digital pathology samples analyzed by the QA machine learning model and/or the historical comparison results.

According to an implementation, the output of the comparison results at 234 may be or may include a visual indicator. The visual indicator may be provided, for example, via the viewing application tool 108 of FIG. 1B. The visual indicator may identify a given difference by, for example, highlighting biomarkers used to generate the disease designation, attributes of the slide contributing to the disease designation, or the like.

According to an implementation, the QA machine learning algorithm may also be trained based on and/or receive as inputs clinical information (e.g. patient information, surgical information, diagnostic information, etc.), laboratory information (e.g. processing times, personnel, tests, etc.). The QA machine learning algorithm may provide a quality designation based on such inputs. Additionally, the QA machine learning algorithm may provide alternative or additional outputs such as a processing score, a personnel evaluation, or the like.

As further disclosed herein, the QA machine learning algorithm and/or the comparison results may be integrated within a pipeline of a clinical workflow for generating, analyzing, and/or reviewing digital pathology images.

Figure 4:
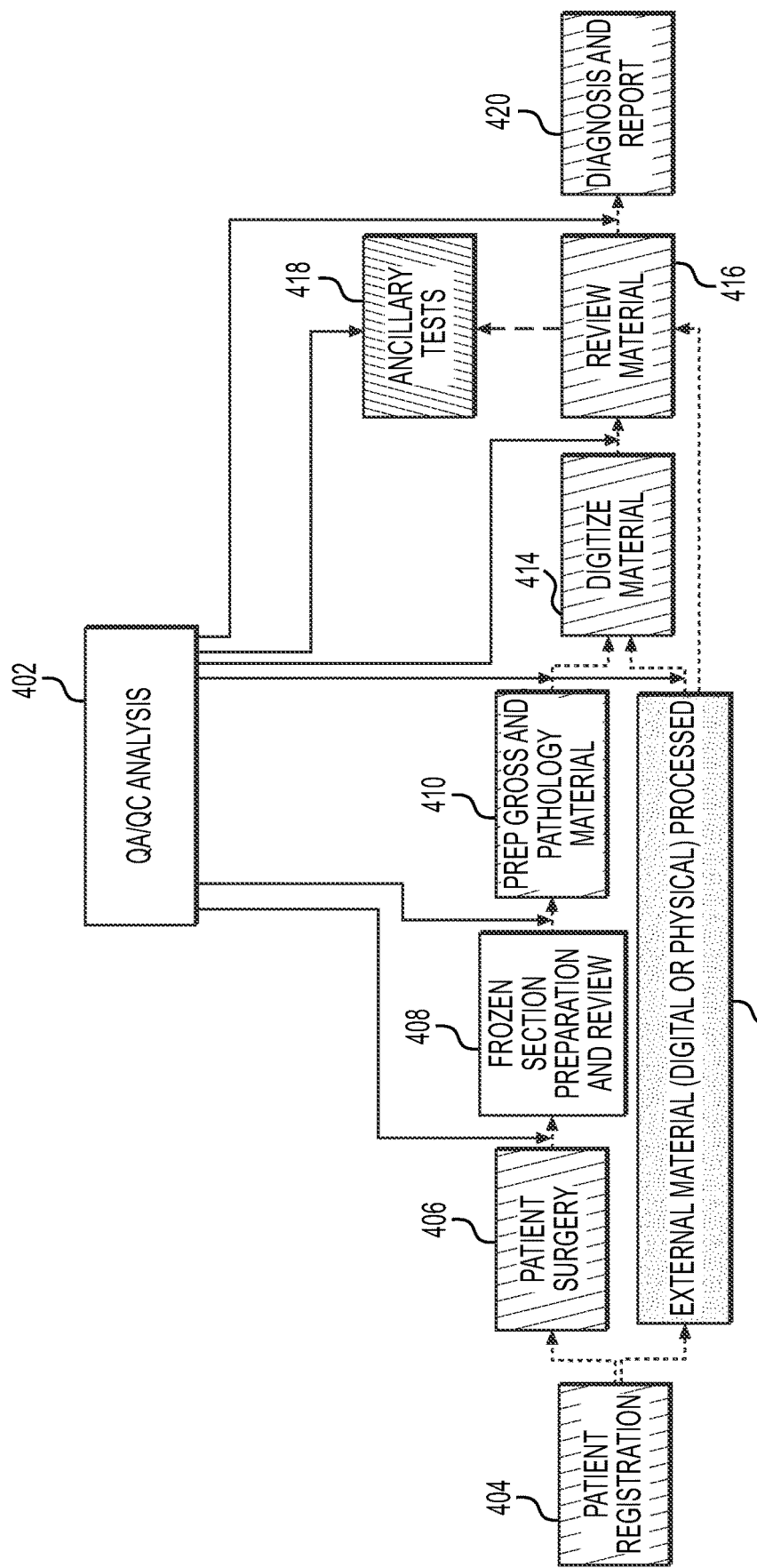
FIG. 4 illustrates a diagram for implementing QA/QC analysis at different stages of a diagnosis, according to an exemplary embodiment of the present disclosure.

FIG. 4 is a diagram that shows a clinical workflow of a detection-based technique. According to implementations of the disclosed subject matter, a QA and/or QC analysis (QA/QC analysis 402), in accordance with the techniques of FIG. 2A (i.e., QC analysis) and/or FIG. 2B (i.e., QA analysis) may be implemented at one or a plurality of points during the workflow. As shown, a patient registration may occur at the beginning of the clinical workflow of the detection-based technique, at 404. The patient registration may include generating a physical or digital patient file that includes or receives patient identification information, patient medical information, and/or other patient related information.

At 406, a patient surgery is conducted. The patient surgery may be a biopsy or cytology that extracts patient tissue from the patient's body. As shown, the QA/QC analysis 402 may occur at or after the patient surgery at 406. For example, an image of a biopsied tissue may be captured and evaluated via the QC analysis of FIG. 2A. The QC analysis of FIG. 2A may provide a quality designation of the biopsied tissue sample such that the system may determine whether a new sample is needed based on the quality designation.

A frozen section preparation and review 408 step may be taken based on the tissue extracted from the patient surgery at 406. Similar to the QA/QC analysis 402 after the patient surgery 406, the QA/QC analysis 402 may occur at or after the frozen section preparation and review 408. For example, an image of a frozen section may be captured and evaluated via the QC analysis of FIG. 2A. The QC analysis of FIG. 2A may provide a quality designation of the frozen section such that the system may determine whether a new frozen section is needed based on the quality designation.

Pathology material preparation 410 (e.g., staining a sample) may occur based on the patient surgery at 406 and/or the frozen section preparation and review at 408. Similar to the QA/QC analysis 402 after the patient surgery 406, the QA/QC analysis 402 may occur at or after the pathology material preparation 410. For example, an image of a prepared pathology material may be captured and evaluated via the QC analysis of FIG. 2A. The QC analysis of FIG. 2A may provide a quality designation of the prepared pathology material such that the system may determine whether new prepared pathology material is needed based on the quality designation.

According to an implementation, external material processing 412 may occur as a substitute for the patient surgery 406, frozen section preparation and review 408, and pathology material preparation 410. The external material processing 412 may be based on a digital or physical sample that may be previously obtained or provided by a third-party. Similar to the QA/QC analysis 402 after the patient surgery 406, the QA/QC analysis 402 may occur based on the external material processing 412.

Digitized material 414 may be generated based on either the pathology material preparation 410 or the external material processing 412. Similar to the QA/QC analysis 402 after the patient surgery 406, the QA/QC analysis 402 may occur based on the digitized material 414.

Review material 416 may be generated based on either the digitized material 414 or the external material processing 412. Similar to the QA/QC analysis 402 after the patient surgery 406, the QA/QC analysis 402 may occur based on the review material 416. For example, an image used for the review material 416 may be captured and evaluated via the QC analysis of FIG. 2A. The QC analysis of FIG. 2A may provide a quality designation of the image such that the system may determine whether a new frozen section is needed based on the quality designation. As another example, an initial diagnosis may be made based on the review material 416 and/or ancillary tests 418. The QA analysis of FIG. 2B may provide a comparison result between the initial diagnosis and a disease diagnoses generated by a QA machine learning model such that a notification may be generated to indicate an artifact and/or difference indicated by the comparison.

A diagnosis and report 420 may be generated at the conclusion of the workflow provided in FIG. 4. Similar to the QA/QC analysis at each of the steps of FIG. 4, a QA/QC analysis 402 may occur based on the diagnosis and report 420, in accordance with FIGS. 2A and 2B herein.

Figure 5:
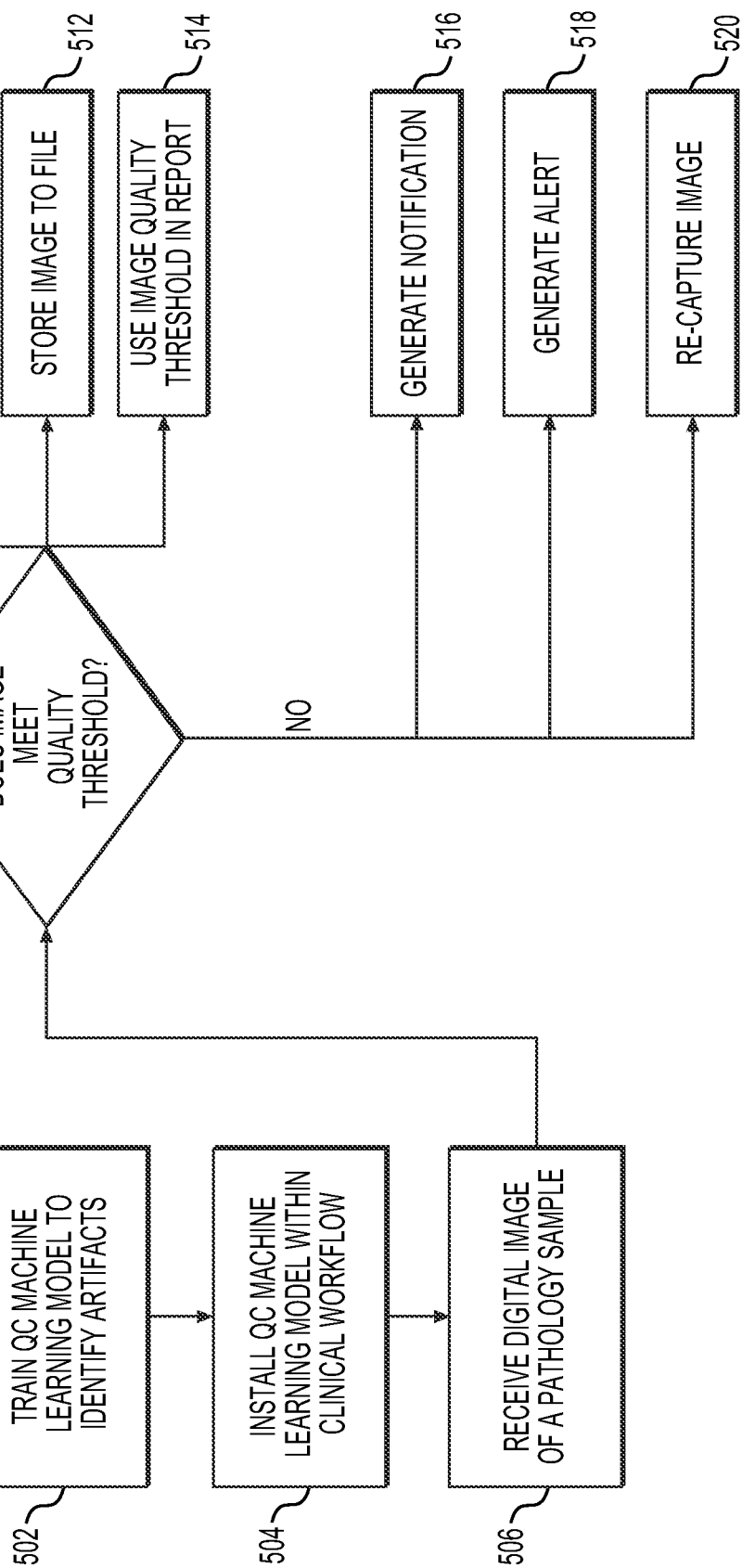
FIG. 5 is a flowchart of an exemplary embodiment of a QC implementation, according to an exemplary embodiment of the present disclosure.
Figure 6:
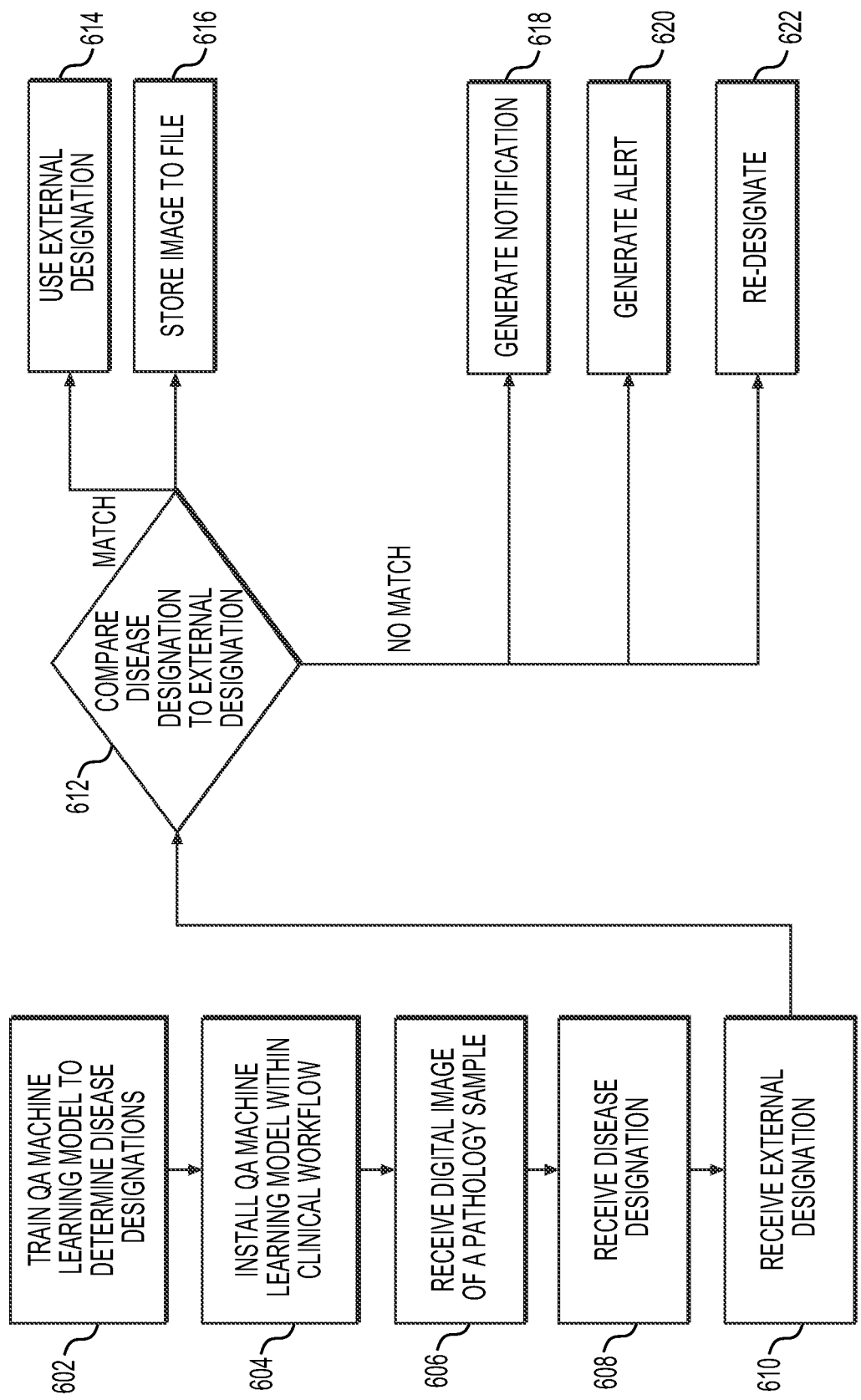
FIG. 6 is a flowchart of an exemplary embodiment of a QA implementation, according to an exemplary embodiment of the present disclosure.
Figure 7:
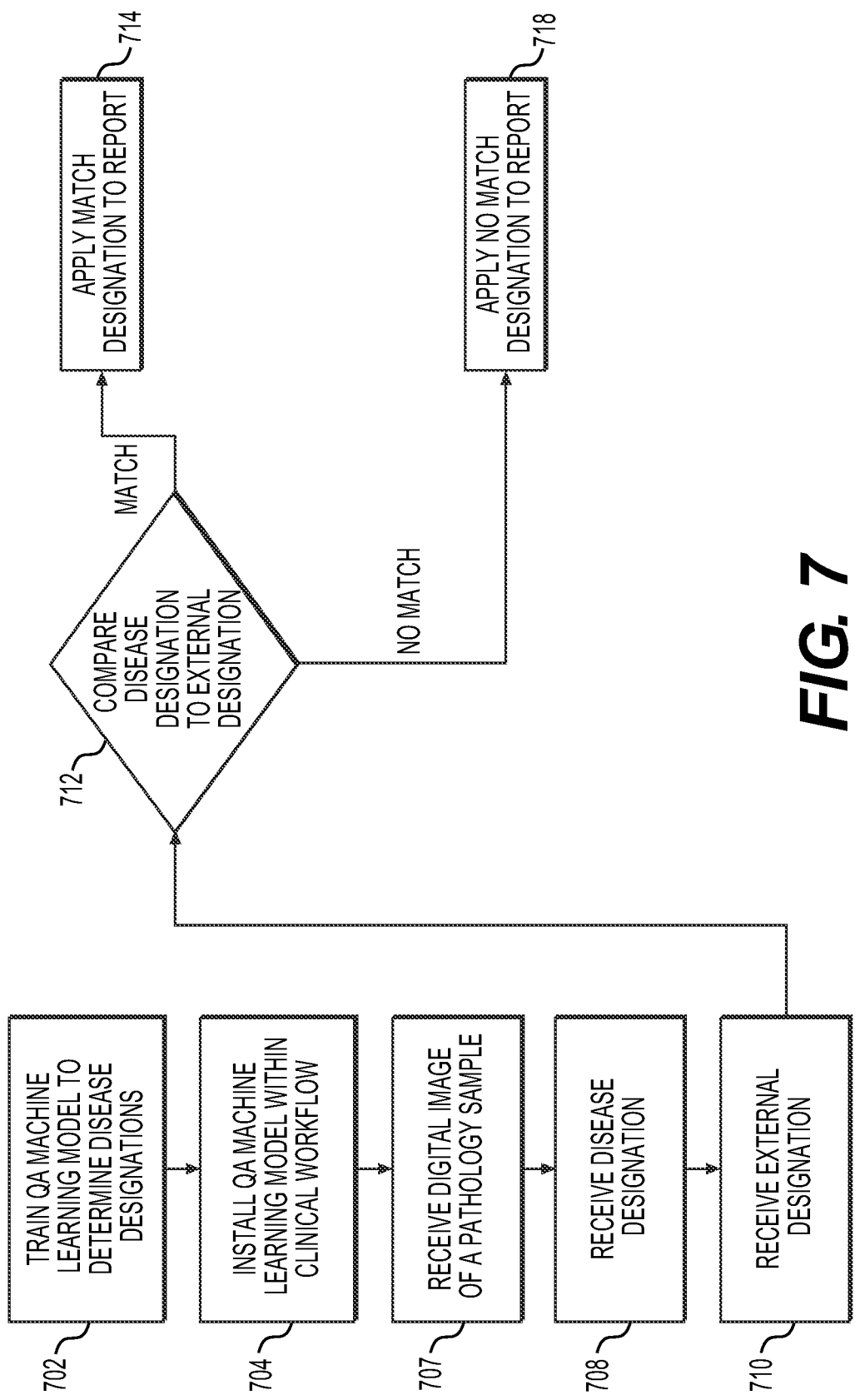
FIG. 7 is a flowchart of an exemplary embodiment of another QA implementation, according to an exemplary embodiment of the present disclosure.

FIGS. 5-7 show example implementations of the QA/QC analysis as disclosed herein in reference to FIGS. 2A and 2B. FIG. 5 shows a flowchart wherein the quality of a prepared pathology specimen is controlled after digitizing the pathology images. At 502, a QC machine learning model may be trained to identify artifacts. The training may be conducted with images of a pathology specimen (e.g. histology, cytology, frozen section, etc.), and an indication of whether the image contains scanning artifacts or errors (e.g. blur, missing tissue, lines, etc.) or artifacts from tissue preparation (e.g. missing or folded tissue, bubbles, cracks in glass, scratches, dust, pen, over stain, etc.) that can negatively impact diagnostic quality.

At 504, the QC machine learning model may be installed within one or more aspects of a clinical workflow/pipeline such as in a network drive, workstation, image storage device, virtual machine or directly integrated into the scanner. The installation may be deployed on-premises or remote (e.g., cloud based). As an example, the QC machine learning may be integrated within a scanner software such that all digital scans are passed through the QC machine learning and the techniques disclosed in reference to FIG. 2A.

At 506, a digital image of a pathology sample (e.g. histology, cytology, frozen section, etc.) may be received and stored locally or remotely. The QC machine learning model of 504 may determine whether an image has scanning or tissue preparation artifacts and, optionally, which type of error.

At 508, a quality designation may be made, by the QC machine learning model of 504, regarding whether the image meets a quality threshold. The quality designation may be made based on one or more inputs provided to the QC machine learning model. If the quality designation meets or exceeds a quality threshold (i.e., the "Yes" branch), then the digital image of 506 may be used for diagnosis at 510, may be stored to a file as an image that meets the quality threshold at 512, and/or the image quality threshold met by the image may be used in a report at 514. According to an implementation, though not shown in FIG. 5, a notification may be generated when a digital image meets the quality threshold to indicate a successful image capture.

If the quality designation does not meet the quality threshold (i.e., the "No" branch), then a notification may be generated at 516 indicating the same. For example, the notification may be provided to an applicable health care professional such as a histology technician with an indication of which specimen needs to be re-prepared. Alternatively, or in addition, a scanner operator may be notified to rescan the material. Additionally, an alert may be generated at 518. The alert may be generated, for example, if the degree to which the digital image does not meet the quality threshold is significant. A visual indicator may also be provided to one or more users and may include information about what, where, and/or why the digital image did not meet the quality threshold. The digital image may be re-captured at 520.

The result of 508 regarding whether the digital image did or did not meet the quality threshold may be associated with a patient file or the specimen's history in, for example, a laboratory information system.

A report may be generated based on the result of 508 and may include types of errors found, number of errors found for each type, clinical impact of errors, time taken to rectify errors, potential patterns or correlations in errors such as whether a particular scanner tends to generate errors, a particular staining type which tends to generate errors, a particular tissue source which tends to generate errors, or the likes. As disclosed herein, the errors may be or may be a type of artifact.

FIG. 6 shows a flowchart for generating and applying comparison results by comparing a disease diagnosis and an external diagnosis, as discussed in relation to FIG. 2B. The implementation shown in FIG. 6 may be, for example, a QA implementation prior to a sign-out or final diagnosis. Based on the process shown in FIG. 6, the quality of a slide assessment through a pathologist may be assured before the case is signed-out. At 602, a QA machine learning model may be trained to identify biomarkers for determination of cancer detection, cancer grade, cancer origin, diagnosis, a presence or absence of a microorganism, specimen type, cancer type, cancer status, tumor size, lesions risk level, grade, or the like. The training may be conducted with images of a pathology specimen (e.g. histology, cytology, frozen section, etc.), patient associated information, as disclosed herein, and an indication of known biomarkers, or disease designations.

At 604, the QA machine learning model may be installed within one or more aspects of a clinical workflow/pipeline such as in a network drive, workstation, image storage device, virtual machine, or report analysis. The model may be deployed with logic to manage concordances and discordances. The installation may be deployed on-premises or remote (e.g., cloud based). As an example, the QA machine learning model may be integrated within a report module such that it receives, as an input, the external designation provided via a report (e.g., a pathologist's report).

At 606, a digital image of a pathology sample (e.g. histology, cytology, frozen section, etc.) may be received and stored locally or remotely. The QA machine learning model of 604 may generate a disease designation at 608, which may include one or more elements of a diagnostic determination (e.g., cancer detection, cancer grade, cancer origin, diagnosis, a presence or absence of a microorganism, specimen type, cancer type, cancer status, tumor size, lesions risk level, grade, etc.). The disease designation may be output to a local or remote storage. At 610, an external designation may be received from a manual designation (e.g., by a pathologist) or an automated designation (e.g., by a third-party system, a different machine learning system, or a computer algorithm).

At 612, the disease designation of 608 may be compared to the external designation of 610 to output a "Match", a "No Match" or a degree of either of the same. As shown via the Match branch, if the disease designation and the external designation match, the external designation may be cleared and used as an authoritative designation at 614. The digital image may also be stored to file for future use, analysis, or reference at 616. Additionally, the disease designation and/or external designation may be associated with a patient file or specimen file and stored accordingly.

As shown via the No Match branch, if the disease designation and the external designation do not match, a notification may be generated at 618. The notification may be provided to any applicable individuals or devices, such as to a primary pathologist prior to the respective case being signed out. Accordingly, the notification may be generated at 618 if the external diagnosis entered is different from the disease diagnosis determined by the QA machine learning model, where the external diagnosis may be entered into a laboratory information system, may be provided by an external institution (e.g., a diagnostic consultation, second opinion, transferred case, etc.), or a pathologist's diagnosis. Based on a mismatch between the disease designation and the external designation, a visual indicator may be provided to show what, where, and/or why a discordance was found.

At 620, an alert may be generated based on the No Match determination if, for example, the degree of difference between the disease diagnosis and the external diagnosis exceeds a threshold, based on the type of mismatch, or the like. Additionally, at 622, a re-designation of the digital image or corresponding specimen may be initiated based on the mismatch between the disease diagnosis and the external diagnosis.

According to an implementation, both the disease diagnosis and the external diagnosis may be provided via a final diagnostic report. Additionally, periodic retrospective reports for review may be generated. Such reports may be generated per health care professional, per technician, per site, per institution, or the like. The reports may include one or more of types of discordances, types of concordances, number of discordances rectified to be concordant, discordances and any relevant follow-up information available for the patient.

FIG. 7 shows a flowchart for generating and applying comparison results by comparing a disease diagnosis and an external diagnosis, as discussed in relation to FIG. 2B. The implementation shown in FIG. 7 may be, for example, a QA implementation after a sign-out or final diagnosis and may facilitate report generation based on one or more diagnosis. Based on the process shown in FIG. 7, the quality of a slide assessment through a pathologist may be assured after the case is signed-out. At 702, a QA machine learning model may be trained to identify biomarkers for determination of cancer detection, cancer grade, cancer origin, diagnosis, a presence or absence of a microorganism, specimen type, cancer type, cancer status, tumor size, lesions risk level, grade, or the like. The training may be conducted with images of a pathology specimen (e.g. histology, cytology, frozen section, etc.), patient associated information, as disclosed herein, and an indication of known biomarkers, or disease designations.

At 704, the QA machine learning model may be installed within one or more aspects of a clinical workflow/pipeline such as in a network drive, workstation, image storage device, virtual machine, or report analysis. The model may be deployed with logic to manage concordances and discordances. The installation may be deployed on-premises or remote (e.g., cloud based). As an example, the QA machine learning model may be integrated within a report module such that it receives, as an input, the external designation provided via a report (e.g., a pathologist's report).

At 707, a digital image of a pathology sample (e.g. histology, cytology, frozen section, etc.) may be received and stored locally or remotely. The QA machine learning model of 704 may generate a disease designation at 708, which may include one or more elements of a diagnostic determination (e.g., cancer detection, cancer grade, cancer origin, diagnosis, a presence or absence of a microorganism, specimen type, cancer type, cancer status, tumor size, lesions risk level, grade, etc.). The disease designation may be output to a local or remote storage. At 710, an external designation may be received from a manual designation (e.g., by a pathologist) or an automated designation (e.g., by a third-party system, a different machine learning system, or a computer algorithm).

At 712, the disease designation of 708 may be compared to the external designation of 710 to output a "Match", a "No Match" or a degree of either of the same. Based on a Match or No Match designation, the steps shown in FIG. 6 may be implemented. Additionally, a Match designation may be applied to a report at 714 and a No Match designation may be applied to a report at 718. The report may include attributes of the Match or No Match designations such as degrees of discord or concord, specific areas of discord or concord, or the like.

Additionally, one or more elements of an external designation for one or more cases may be compared to corresponding one or more elements of the disease designation by the QA machine learning model, and the comparison of such results may be provided via the report. Such a comparison may be conducted across multiple cases. For example, the comparison results from 712 may be provided to all cases or all cases from a certain tissue type, diagnosed by a certain pathologist, coming from a certain clinician, patients with a certain insurance, patients with a certain demographic type, from a certain site for the preceding time period (e.g., six months), or the like. The results from one or more such comparisons may be included in a report to highlight concordances, discordances, and the degrees of the same as categorized by case type, tissue type, individual, patient, insurance, demographic, site, or time period. Accordingly one or more reports may be retrospective and may be generated per-pathologist, per-technician, per-site, per-tissue type, per-stain, per-scanner, per-image type, per-sample preparation, per-diagnosis, per-demographic element, per-insurance carrier, per-referring physician and/or per institution, or the like. The reports may include one or more of types of discordances, types of concordances, number of discordances rectified to be concordant, discordances and any relevant follow-up information available for the patient, and any other individual or aggregate measure of discordance or discrepancy between the disease diagnosis by the QA machine learning model and external diagnosis.

The one or more reports may be provided to one or more individuals, administrators, insurance companies, governing bodies, clinicians, or the like and may include rates (e.g., concordance rates, discordance rates, etc.) and/or other measures of quality derived from the comparison of the disease diagnosis by the QA machine learning model and the external diagnosis.

Figure 8:
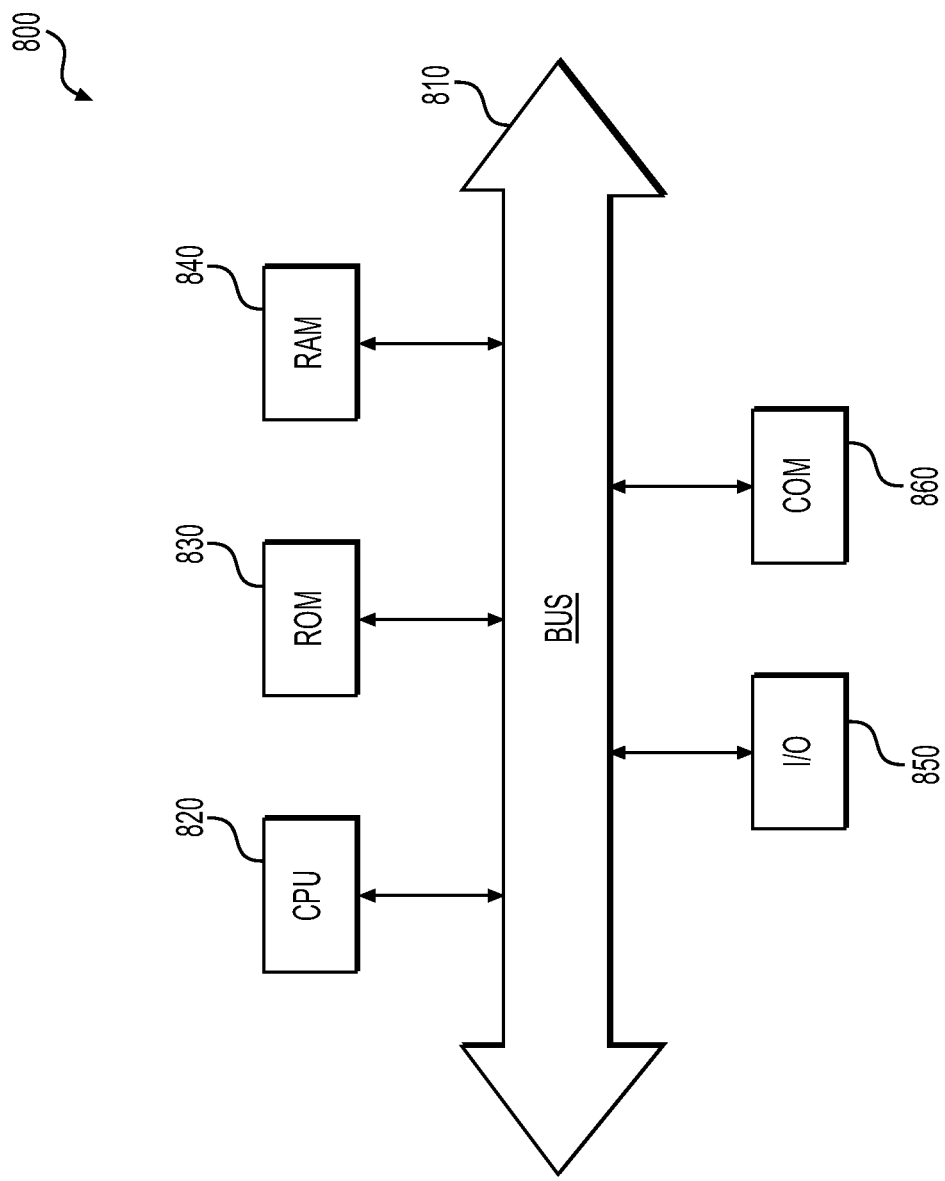
FIG. 8 depicts an example system that may execute techniques presented herein.

As shown in FIG. 8, device 800 may include a central processing unit (CPU) 820. CPU 820 may be any type of processor device including, for example, any type of special purpose or a general-purpose microprocessor device. As will be appreciated by persons skilled in the relevant art, CPU 820 also may be a single processor in a multi-core/multi-processor system, such system operating alone, or in a cluster of computing devices operating in a cluster or server farm. CPU 820 may be connected to a data communication infrastructure 810, for example, a bus, message queue, network, or multi-core message-passing scheme.

Device 800 also may include a main memory 840, for example, random access memory (RAM), and may include a secondary memory 830. Secondary memory 830, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include other similar means for allowing computer programs or other instructions to be loaded into device 800. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 800.

Device 800 also may include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical, or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 800 also may include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. A computer-implemented method for processing electronic images, the method comprising:
   receiving a digital image corresponding to a target specimen associated with a pathology category, wherein the digital image is an image of human or animal tissue and/or an image algorithmically generated to replicate human or animal tissue;
   determining a quality control (QC) machine learning model, the QC machine learning model being configured to predict a quality designation based on a presence or lack of one or more artifacts and/or;
   providing the digital image as an input to the QC machine learning model;
   receiving the quality designation associated with the digital image as an output from the QC machine learning model;
   determining, based on the output from the QC machine learning model, whether the quality designation is either an approved designation or a rejected designation, wherein the quality designation is indicative or artifacts such as errors or imperfections in the digital image, wherein the quality designation includes an approval scale and/or a rejection scale that provides a finer indication of the image quality;
   determining a quality assurance (QA) machine learning model configured to predict a disease designation based on one or more biomarkers, the QA machine learning model being different than the QC machine learning model;
   providing the digital image to the QA machine learning model;
   receiving a disease designation for the digital image as an output from the QA machine learning model;
   receiving an external designation for one of the digital image or the target specimen and comprising a disease property selected from at least one of a cancer detection, a cancer grade, a cancer origin, a diagnosis, a presence or absence of a microorganism, a specimen type, a cancer type, a cancer status, a tumor size, a lesions risk level, or a grade;
   evaluating the external designation by comparing the disease designation to the external designation;
   outputting a comparison result based on evaluating the external designation by comparing the disease designation to the external designation; and
   rejecting the external designation based on the evaluation, based on the external designation deviating from the disease designation beyond a predetermined threshold.

2. The computer-implemented method of claim 1, wherein outputting the quality designation of the digital image further comprises generating a report comprising at least one of a type of artifact found, a number of artifacts found, clinical impact of an artifact found, a time to rectify an artifact, potential pattern, or correlation in a plurality of artifacts.

3. The computer-implemented method of claim 1, wherein the pathology category is one of histology, cytology, frozen section, or immunohistochemistry.

4. The computer-implemented method of claim 2, wherein the quality designation includes a quality score determination.

5. The computer-implemented method of claim 1, further comprising automatically generating a notification based on quality characteristic, the notification comprising an artifact presence, absence, or degree designation.

6. The computer-implemented method of claim 1, wherein outputting the quality designation of the digital image further comprises a visual indicator corresponding to an artifact of the digital image.

7. The computer-implemented method of claim 1, wherein the QA machine learning model is generated by processing a plurality of training images, associated with the pathology category, to predict a disease designation based on one or more biomarkers.

8. The computer-implemented method of claim 1, wherein the one or more artifacts comprise a missing tissue, a glass crack, a bubble, a blur amount, a missing tissue, a folded tissue, a line, a scratch, dust, pen, or a stain amount.

9. A system for processing electronic images, the system comprising:
   at least one memory storing instructions; and
   at least one processor executing the instructions to perform operations comprising:
      receiving a digital image corresponding to a target specimen associated with a pathology category, wherein the digital image is an image of human or animal tissue and/or an image algorithmically generated to replicate human or animal tissue;

determining a quality control (QC) machine learning model, the QC machine learning model being configured to predict a quality designation based on a presence or lack of one or more artifacts and/or;

providing the digital image as an input to the QC machine learning model;

receiving the quality designation associated with the digital image as an output from the QC machine learning model;

determining, based on the output from the QC machine learning model, whether the quality designation is either an approved designation or a rejected designation, wherein the quality designation is indicative or artifacts such as errors or imperfections in the digital image, wherein the quality designation includes an approval scale and/or a rejection scale that provides a finer indication of the image quality;

determining a quality assurance (QA) machine learning model configured to predict a disease designation based on one or more biomarkers, the QA machine learning model being different than the QC machine learning model;

providing the digital image to the QA machine learning model;

receiving a disease designation for the digital image as an output from the QA machine learning model;

receiving an external designation for one of the digital image or the target specimen and comprising a disease property selected from at least one of a cancer detection, a cancer grade, a cancer origin, a diagnosis, a presence or absence of a microorganism, a specimen type, a cancer type, a cancer status, a tumor size, a lesions risk level, or a grade;

evaluating the external designation by comparing the disease designation to the external designation;

outputting a comparison result based on evaluating the external designation by comparing the disease designation to the external designation; and rejecting the external designation based on the evaluation, based on the external designation deviating from the disease designation beyond a predetermined threshold.

10. The system of claim 9, wherein outputting the quality designation of the digital image further comprises generating a report comprising at least one of a type of artifact found, a number of artifacts found, clinical impact of an artifact found, a time to rectify an artifact, potential pattern, or correlation in a plurality of artifacts.

11. The system of claim 9, wherein the pathology category is one of histology, cytology, frozen section, or immunohistochemistry.

12. The system of claim 9, wherein the quality designation includes a quality score determination.

13. The system of claim 9, further comprising automatically generating a notification based on quality characteristic, the notification comprising an artifact presence, absence, or degree designation.

14. The system of claim 9, wherein outputting the quality designation of the digital image further comprises a visual indicator corresponding to an artifact of the digital image.

15. The system of claim 9, wherein the QA machine learning model is generated by processing a plurality of training images, associated with the pathology category, to predict a disease designation based on one or more biomarkers.

16. The system of claim 9, wherein the one or more artifacts comprise a missing tissue, a glass crack, a bubble, a blur amount, a missing tissue, a folded tissue, a line, a scratch, dust, pen, or a stain amount.

17. A non-transitory computer-readable medium storing instructions that, when executed by a processor, perform operations processing electronic medical images, the operations comprising:

receiving a digital image corresponding to a target specimen associated with a pathology category, wherein the digital image is an image of human or animal tissue and/or an image algorithmically generated to replicate human or animal tissue;

determining a quality control (QC) machine learning model, the QC machine learning model being configured to predict a quality designation based on a presence or lack of one or more artifacts and/or;

providing the digital image as an input to the QC machine learning model;

receiving the quality designation associated with the digital image as an output from the QC machine learning model;

determining, based on the output from the QC machine learning model, whether the quality designation is either an approved designation or a rejected designation, wherein the quality designation is indicative or artifacts such as errors or imperfections in the digital image, wherein the quality designation includes an approval scale and/or a rejection scale that provides a finer indication of the image quality;

determining a quality assurance (QA) machine learning model configured to predict a disease designation based on one or more biomarkers, the QA machine learning model being different than the QC machine learning model;

providing the digital image to the QA machine learning model;

receiving a disease designation for the digital image as an output from the QA machine learning model;

receiving an external designation for one of the digital image or the target specimen and comprising a disease property selected from at least one of a cancer detection, a cancer grade, a cancer origin, a diagnosis, a presence or absence of a microorganism, a specimen type, a cancer type, a cancer status, a tumor size, a lesions risk level, or a grade;

evaluating the external designation by comparing the disease designation to the external designation;

outputting a comparison result based on evaluating the external designation by comparing the disease designation to the external designation; and rejecting the external designation based on the evaluation, based on the external designation deviating from the disease designation beyond a predetermined threshold.

18. The non-transitory computer-readable medium of claim 17, wherein outputting the quality designation of the digital image further comprises generating a report comprising at least one of a type of artifact found, a number of artifacts found, clinical impact of an artifact found, a time to rectify an artifact, potential pattern, or correlation in a plurality of artifacts.

19. The computer-implemented method of claim 1, wherein the one or more artifacts is a blur, missing tissue, line, folded tissue, bubbles, cracks in glass, scratches, dust, pen marking, and/or stains of the digital image.

20. The computer-implemented method of claim 1, further concluding:
determining, using the QC machine learning model, a report based on the quality designation, the report including types of artifacts found, number of each type of artifact, clinical impact of artifacts, time to rectify artifact, and/or potential patterns or correlations in artifacts.

* * * * *